(12) United States Patent
Chan et al.

(10) Patent No.: US 9,861,514 B2
(45) Date of Patent: Jan. 9, 2018

(54) APPARATUS FOR STORING AND DISPENSING CONDOM WRAPPERS

(71) Applicant: Rulin Chen, Guangzhou, Guangdong (CN)

(72) Inventors: Victor W. J. Chan, Taipo (HK); Genie Geraldine Lam, Taipo (HK)

(73) Assignees: Victor W.J. Chan, New Territories (HK); Rulin Chen, Guangdong (CN)

( * ) Notice: Subject to any disclaimer, the term of this patent is extended or adjusted under 35 U.S.C. 154(b) by 168 days.

(21) Appl. No.: 14/735,919

(22) Filed: Jun. 10, 2015

(65) Prior Publication Data

US 2016/0074208 A1  Mar. 17, 2016

(30) Foreign Application Priority Data

Sep. 12, 2014 (CN) .......................... 2014 1 0465543

(51) Int. Cl.
*A61F 6/00* (2006.01)
*A61F 6/04* (2006.01)

(52) U.S. Cl.
CPC ................. *A61F 6/005* (2013.01); *A61F 6/04* (2013.01)

(58) Field of Classification Search
CPC .... A61F 6/005; A61F 6/04; A61F 6/02; A61F 6/06; A61F 2006/049; A61F 2006/041; A61F 6/00; A47K 10/24; B65D 83/08
See application file for complete search history.

(56) References Cited

U.S. PATENT DOCUMENTS

| 3,324,754 | A |   | 6/1967  | Peavy    |             |
|-----------|---|---|---------|----------|-------------|
| 5,673,541 | A | * | 10/1997 | Arzuman  | B65B 43/465 |
|           |   |   |         |          | 53/284.7    |
| 5,806,278 | A | * | 9/1998  | Shelledy | B65D 83/08  |
|           |   |   |         |          | 414/412     |
| 7,246,720 | B1|   | 7/2007  | Montoya  |             |
| 7,246,729 | B2|   | 7/2007  | Montoya  |             |

FOREIGN PATENT DOCUMENTS

CA        2130536 A1    2/1996

* cited by examiner

*Primary Examiner* — Jonathan Riley
*Assistant Examiner* — Liang Dong
(74) *Attorney, Agent, or Firm* — Berliner & Associates

(57) ABSTRACT

As apparatus for storing and dispensing condoms is provided. The apparatus comprises a body includes a base for receiving a stack of condom wrappers, and an opening for accessing a condom wrapper, the opening including a guide for adjacent a side of the opening. The apparatus also includes a cutting assembly having a blade configurable in an extended position for cutting an edge of the condom wrapper as the condom wrapper is pulled through the opening. The guide configured to deform and/or displace a condom within the condom wrapper laterally away from the blade so that the blade does not cut the condom as the condom wrapper is pulled through the opening, wherein the guide has a gap with a gap height less than a thickness of a rolled condom and wherein at least a portion of the gap is closer to a center of the opening than the blade.

7 Claims, 8 Drawing Sheets

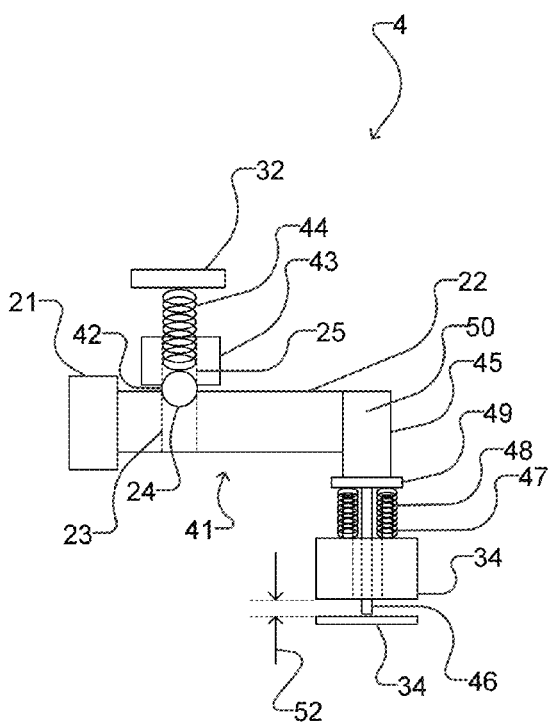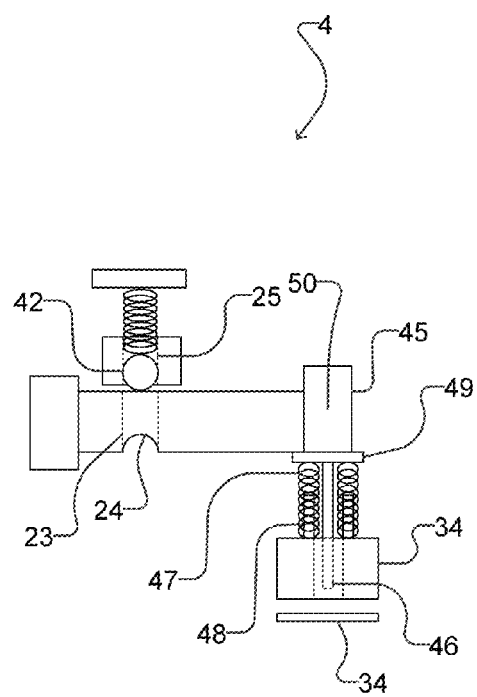
Fig. 1B                               Fig. 1C

APPARATUS FOR STORING AND DISPENSING CONDOM WRAPPERS

TECHNICAL FIELD

This invention relates to apparatus for storing and dispensing condom wrappers.

BACKGROUND

Condom packaging typically comprises a single condom packed in an individual wrapper, which is linked together with other wrappers and packed in a box. To access a condom, a user opens the box, separates an individual wrapper from a link of wrappers, tears open the wrapper, removes the condom from the wrapper, and inspects the condom to determine its correct orientation before use. Many of these steps have the potential for damaging or contaminating the condom and creating barriers for users Condom packaging typically requires significant packaging for retail and logistical purposes. Each box of condoms is typically packed in packs of twelve into an intermediate box, and packs of intermediate boxes are in turn packed into a carton for delivery in large quantities. The significant packaging leads to significant waste of materials.

Improved apparatus for storing and dispensing condoms that address ax least some of the foregoing issues are desirable.

SUMMARY

The inventions described herein have many aspects, some of which relate to apparatus for storing and dispensing condoms.

According to one aspect, an apparatus for storing and dispensing condoms is provided. The apparatus comprises a body comprising a base for receiving a stack of condom wrappers, and an opening for accessing a condom wrapper, the opening comprising a guide adjacent a side of me opening. The apparatus also comprises a culling assembly comprising a blade configurable in an extended position for cutting an edge of the condom wrapper as the condom wrapper is pulled through the opening. The guide is configured to deform and/or displace a condom within she condom wrapper laterally away from the blade so that the blade does not cut the condom, as the condom wrapper is pulled through the opening, wherein the guide comprising a gap with a gap height less than a thickness of a rolled condom and wherein at least a portion of the gap is closer to a center of the opening than the blade.

The gap height may be between 0.2 mm to 2.0 mm or 0.5 mm to 1.5 mm.

The guide may define an entrance facing an interior of the body, the entrance comprising a slanted surface defining an entrance height greater than the gap height to facilitate entry of the condom wrapper into the guide.

The cutting assembly may be configurable in a retracted position for avoiding cutting the edge of the condom wrapper as the condom wrapper is pulled through the opening.

The body may comprise a front panel, the front panel comprising the opening.

The opening of the front panel may comprise an expanded portion for facilitating insertion of a user's fingers.

The cutting assembly may comprise a knob comprising: a head disposed outside the body; a barrel fixed to the head and extending into the body through a side aperture of the front panel; and a cam fixed to a distal end of the barrel, the cam comprising a bearing surface abutting a proximal end of the blade, whereby rotation of the knob configures the blade between the extended position and the retracted position.

The barrel may comprise a bearing circumference with at least one recess, and the cutting assembly may further comprise: a stop fixed to the front panel and comprising a through hole; a positioning bah set within the through hole; and a spring for biasing the positioning ball against a bearing circumference of the barrel, the spring comprising a first end bearing against, the positioning ball.

The spring may bias the positioning ball against a recess of the barrel when the knob is rotated to configure the blade at the extended position. The spring may bias the positioning ball against a recess of the barrel when the knob is rotated to configure the blade at the retracted position. The bearing circumference may comprise two opposed recesses, and the spring may bias the positioning ball against a first recess of the barrel when the knob is rotated to configure the blade in the extended position, and against a second recess of the barrel when the knob is rotated to configure the blade in the retracted position.

The apparatus may further comprise at least one spring for biasing the blade into the retracted position, die at least one spring mounted on a guide post fixed on an inner face of the front panel wherein a length of the post is less than an uncompressed length of the at least one spring.

The front panel may comprise a sheath for guiding, extension and retraction of the blade and for stowing the blade in the retracted position.

The blade may comprise a tapered shape with a tip, the tip disposed at a side region of the opening of the front panel when the blade is in the extended position.

The base may comprise a stand extending from a bottom of the body, wherein a height of the base corresponds to a height of the openings of the body and a height of the opening of the front panel such that a user may pull a lowermost condom wrapper from the stack of condom wrappers through the openings of the body and the front panel.

The base may comprise a spring and a plate fixed to a top of the spring, a bottom of the spring fixed to a bottom of the body, wherein a maximum height of the plate corresponds to a height of the openings of the body and a height of the opening of the front panel such that a user may pull an uppermost condom wrapper from the stack of condom wrappers through the openings of the body and the front panel.

The foregoing discussion merely summarizes certain aspects of the inventions and is not intended, nor should it be construed, as limiting the inventions in any way.

BRIEF DESCRIPTION OF DRAWINGS

The accompanying drawings illustrate non-limiting example embodiments of the invention.

FIG. 1B is a front view of a cutting assembly of the embodiment shown in FIG. 1A with the blade in an extended position;

FIG. 1C is a front view of a cutting assembly of the embodiment shown in FIG. 1A with the blade in a retracted position;

DESCRIPTION

Figure 1A:
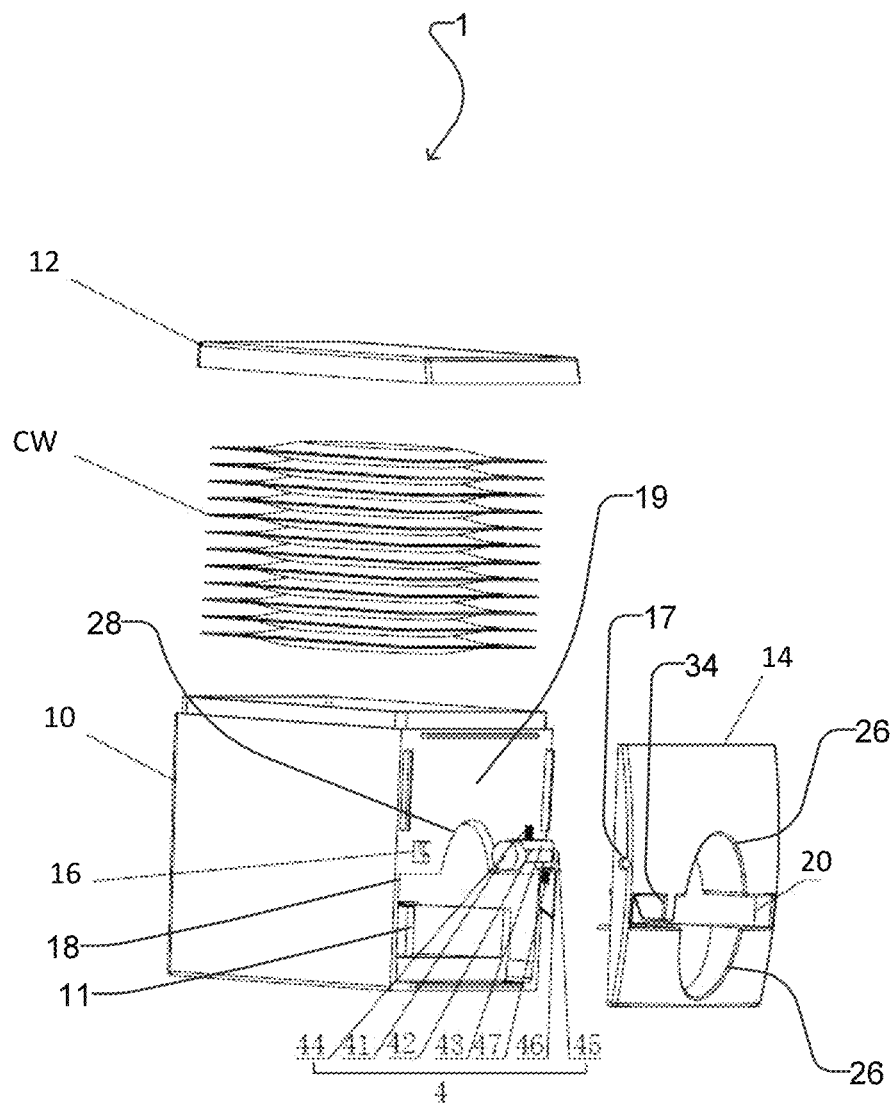
FIG. 1A is an exploded view of an apparatus for storing and dispensing condoms according to an embodiment.
Figure 2:
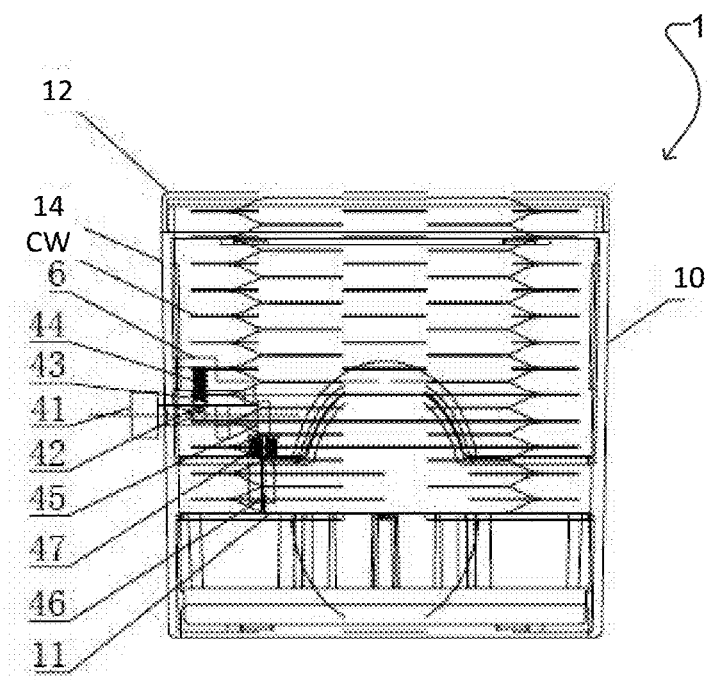
FIG. 2 is a front cutaway view of the embodiment shown in FIG. 1.
Figure 3:
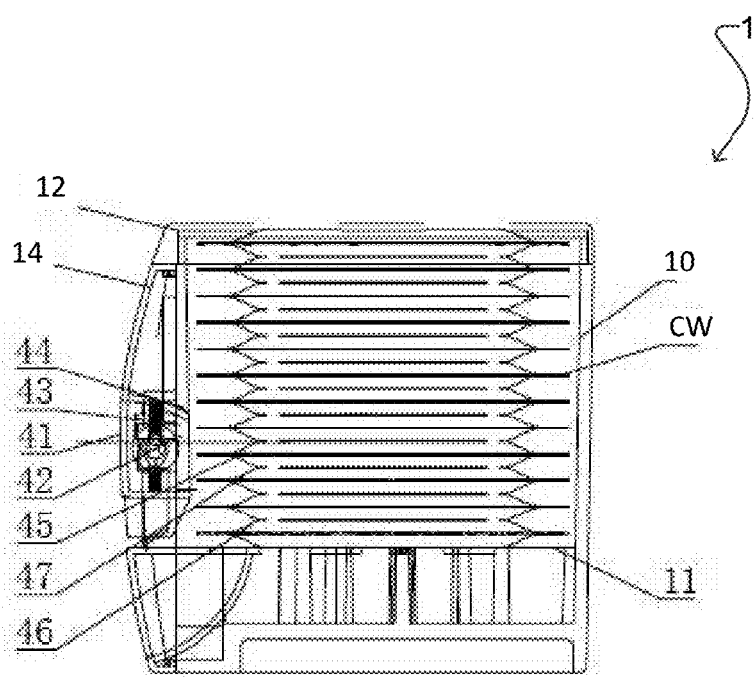
FIG. 3 is a side cutaway view of the embodiment shown in FIG. 1.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The invention relates to apparatus for storing and dispensing condoms. In accordance with one aspect of the invention, a box for storing a stack of condom wrappers is provided. The box includes a retractable blade that cuts open individual condom wrappers in a safe and consistent fashion as it is dispensed from the box.

FIGS. 1 to 7 show a box 1 for storing and dispensing condoms according to one embodiment of the invention. Box 1 comprises a body 10, a top cover 12 and a bottom 13. A base 11 extending upwardly from bottom 13 receives a stack of individual condom wrappers CW which are inserted into box 1 from an open top of body 10. Top cover 12 is placed on body 10 once box 1 is filled with condom wrappers CW.

Body 10 may include a front panel 14 fixedly or detachably attached to a front face 19 of body 10. In some embodiments front panel 14 may be integral with the rest of body 10. In some embodiments, front panel 14 may be absent and features described herein with respect to front panel 14 are instead incorporated into front lace 19 of body 10.

Although box 1 as shown in the illustrated embodiments has a general box shape, in other embodiments box 1 may be of any other shape suitable for storing a stack of condom wrappers CW. Box 1 is generally constructed of a rigid material and is reusable to avoid waste. In some embodiments, box 1 is sized to conveniently fit in a user's hand, allowing a user to grasp box 1 in one hand and remove individual condom wrappers CW, as described further below, with the other hand.

A generally rectangular opening 18 is formed at a lower portion of front face 19 of body 10. A corresponding generally rectangular opening 20 is also formed al a lower portion, of front panel 14.

Openings 18 and 20 are dimensioned to allow a user to pull one condom wrapper CW out of body 10 at a time. In some embodiments, openings 18 and 20 may have expanded portions 26, 28 to allow insertion of user's fingers into box 1 to facilitate grasping a condom wrapper CW in box 1. In an example embodiment, one or more of expanded portions 26, 28 may be semicircular. In some embodiments, base 11 may be a stand 15 having a height that corresponds to the height of openings 18, 20 such that a user may pull a lowermost condom wrapper CW from the stack of condom wrappers CW through openings 18, 20. In some embodiments, the difference between the height of stand 15 and the height of the top of the rectangular portion of opening 18 may be approximately between the thickness of a standard condom wrapper CW and the combined thickness of two standard condom wrappers CW, to allow only one condom wrapper CW to be accessed at a time through opening 18.

A cutting assembly 4 is disposed adjacent opening 20 on front panel 14, in embodiments lacking front panel 14, cutting assembly 4 is disposed, adjacent opening 18 of front face 19 of body 10. Cutting assembly 4 includes a blade 46 configurable in an extended position for cutting an edge of a condom wrapper as the condom wrapper is pulled out of the opening by a user (as best shown in FIG. 1B), and in a retracted position for avoiding cutting the edge of the condom wrapper as the condom wrapper is pulled out of the opening by the user (as best shown in FIG. 1C).

As best shown in FIGS. 1B and 1C, cutting assembly 4 comprises a knob 41 having a head 21, a barrel 22 and a cam 45. Head 21 is located outside of body 10. Barrel 22 is fixed at one end to head 21 and fixed at the other end to cam 45. Barrel 22 extends into body 10 through a side aperture 17 of front panel 14. Barrel 22 is supported by supporting block 31 on an inner face 9 of front panel 14 and supporting block 16 on front face 19 of body 10. Cam 45 is fixed to a distal end of barrel 22. Cam 45 has a bearing surface 50 that bears against blade base 49 of blade 46. As head 21 of knob 41 is rotated by a user, cam 45 rotates, between a maximum stroke (shown in FIG. 1B) and a minimum stroke (shown in FIG. 1C). The maximum stroke configures blade 46 in the extended position and the minimum stroke configures blade 46 in the retracted position.

Blade 46 is biased to retract by way of springs 47 mounted on posts 48. Springs 47 compress as cam 45 approaches its maximum, stroke and decompress as cam 45 approaches it minimum stroke. In other words, springs 47 are biased to push cam 45 towards its minimum stroke and thus blade 46 toward its retracted position. Posts 48 are fixed to either blade base 49 or, as shown in the illustrated embodiment to a portion of if out panel 14 (e.g. guide 34).

Cutting assembly 4 may also have a mechanism for positioning blade 46 in the extended and/or retracted position. Barrel 22 of knob 41 may have at least one recess 24 along a circumferential ball bearing path 23 of barrel 22. Recess 24 is shaped to receive a positioning ball 42. Positioning ball 42 is set within a through hole 25 of a ball stop 43. Positioning ball 42 is biased toward circumferential ball bearing path 23 by one end of a ball spring 44 also set within through hole 25. The other end of ball spring 44 is mounted to or abuts a bracket 32 fixed to an inner face 9 of front panel 14. As head 21 of knob 41 is rotated by a user, positioning ball 42 bears against and along circumferential ball bearing path 23 until positioning ball 42 positions itself in recess 24, temporarily "locking" knob 41 in place. In some embodiments, the position of recess 24 is set to correspond to a rotational position of cam 45 that corresponds with cam 45's maximum stroke (e.g. extended position of blade 46). In other embodiments, the position of 24 is set to correspond to a rotational position of cam 45 that corresponds with cam 45's minimum stroke (e.g. retracted position of blade 46). In other embodiments, circumferential ball bearing path 23 may have two recesses 24, such that spring 44 biases positioning ball 42 against a first recess of barrel 22 when knob 41 is rotated to configure blade 46 in the extended position (maximum stroke of earn 45), and against a second recess of barrel 22 when knob 41 is rotated to configure blade 46 in the retracted position (minimum stroke of cam 45).

Blade 46 may have a taper shape, sued that when blade 46 extends downwards with a gradually reducing cross-section, a tip of blade 46 is disposed at a side of opening 20 of front panel 14 when blade 46 is in the extended position.

Figure 10:
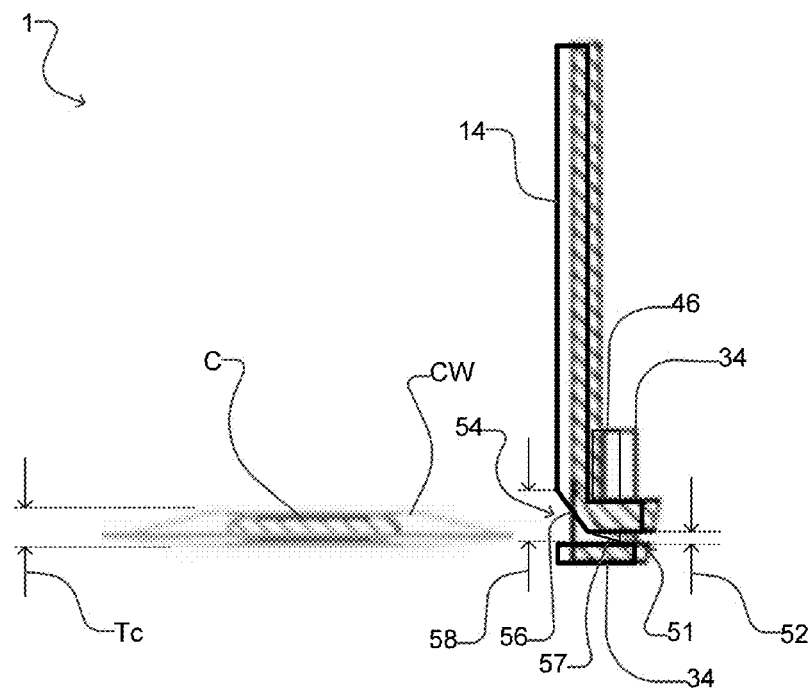
FIG. 10 is a side cutaway view of an opening, guide and blade of the embodiment shown in FIG. 1.

As best shown in FIG. 10, front panel 14 also includes a guide 34. Guide 34 is adjacent a side of opening 20. In embodiments lacking a front panel 14, guide 34 is adjacent a side of opening 18 of front lace 19 and is attached to or integral with front face 19.

Figures 11A, 11B, 11C:
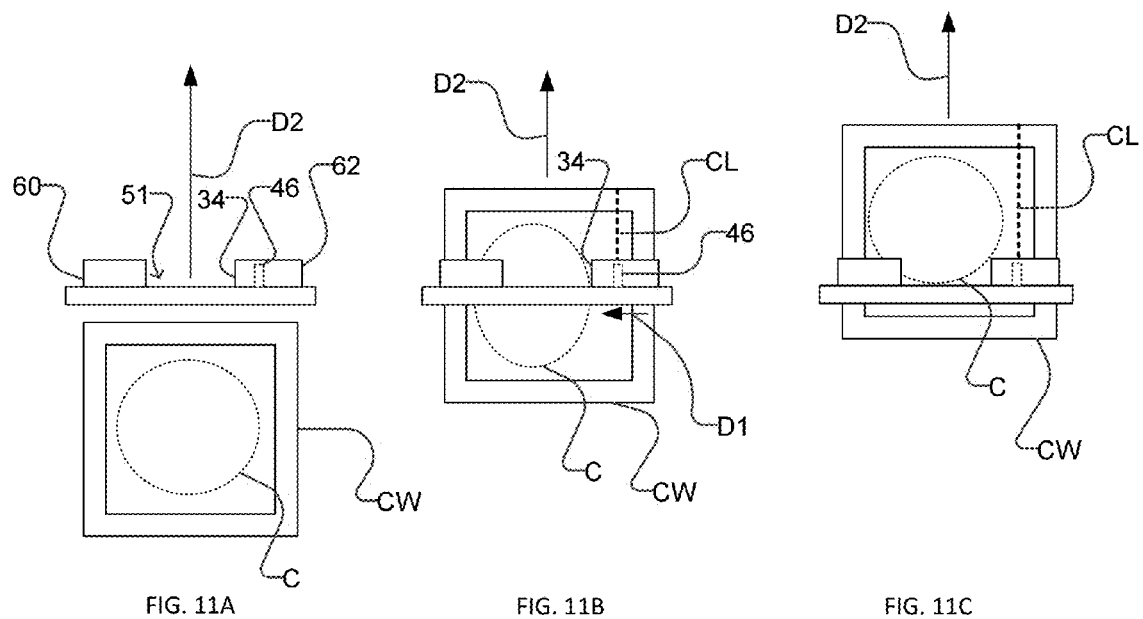
FIGS. 11A, 11B and 11C are top cutaway views of an opening, guide and blade of the embodiment shown in FIG. 1, showing removal of a condom from the apparatus.

Guide 34 ensures accurate cutting action of blade 46. As best shown in FIGS. 11A, 11B and 11C, guide 34 is configured to displace and/or deform condom C within condom wrapper CW laterally away from blade 46 in direction D1 as shown in FIG. 11B so that blade 46 does not cut condom C as condom wrapper CW is pulled through opening 20 by a user in direction D2. As condom wrapper CW is cut along cut line CL by blade 46, condom C reverts to its original form as shown in FIG. 11C. In particular, guide 34 comprises a gap 51 with a gap height 52 less than a thickness $T_c$ of a rolled condom C laid flat as shown in FIG. 10. In some embodiments, gap height 52 may be 0.2 mm to 2.0 mm, or 0.5 mm to 1.5 mm. At least a portion of gap 51 is closer to die center of opening 18, 20 than blade 46. Condom C is deformable within condom wrapper CW along direction D1 because of the inherent deformability of condom C. Condom C is displaceable within condom wrapper CW along direction D1 because of extra room, within condom wrapper CW for condom C to move.

As best shown in FIG. 10, guide 34 also defines an entrance 54 facing an interior of box 1. Entrance 54 is where a side edge of condom wrapper CW enters gap 51. In souse embodiments, entrance 54 comprises a slanted receiving surface 56 defining an entrance height 58 greater than gap height 52 to facilitate entry of condom wrapper CW into gap 51 of guide 34. In the illustrated embodiment, slanted receiving surface 56 defines a lower portion of entrance 54. In some embodiments, slanted receiving surface 56 may define an upper portion of entrance 54, or the upper and lower portions of entrance 54. In some embodiments slanted receiving surface may be curved (e.g. convex) instead of flat.

Guide 34 also shields the user from portions of blade 46 that would otherwise be exposed. Guide 34 ensures only a distal end 57 of blade 46 is exposed and available to cut off a side edge of a condom wrapper CW as it is pulled out of box 1 by a user.

Figure 13:
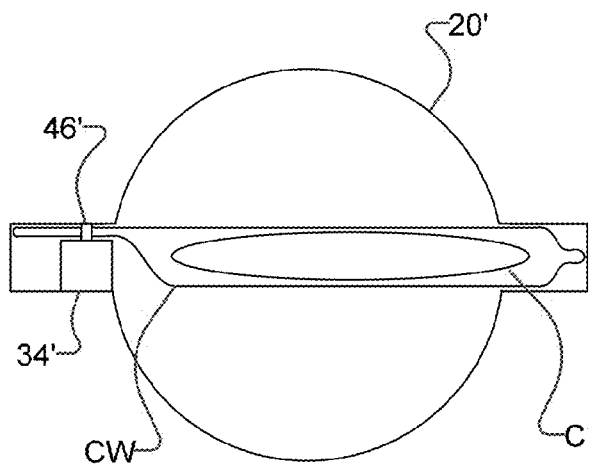
FIG. 13 is a front view of an opening, guide and blade of the embodiment shown in FIG. 8.
Figure 14:
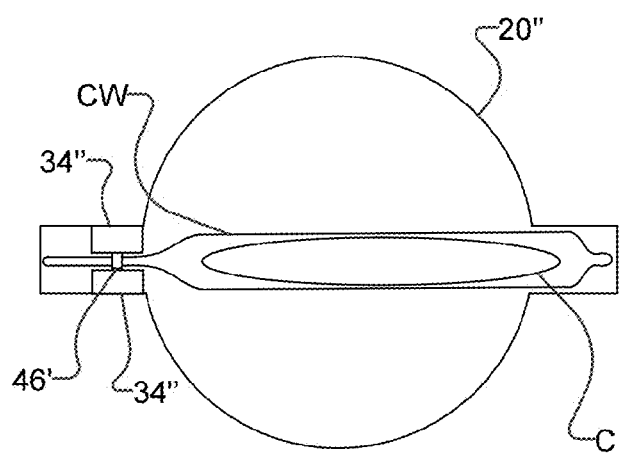
FIG. 14 is a front view of an opening, guide and blade of an apparatus for storing and dispensing condoms according to an embodiment.

FIGS. 13 and 14 illustrate other non-limiting embodiments of guide 34. FIG. 13 shows a guide 34' of a box 1' (as described further below) which projects horn the bottom of the opening; blade 46' extends out of and retracts into guide 34'. FIG. 14 shows guide 34" with two components, one projecting from the bottom of the opening and another projecting from the top of the opening; blade 46" extends out of and retracts into one of the two components. In some embodiments, guide 34 may project from a top or bottom of the opening, and blade 46 may extend out of and retract into the other of the top or bottom of the opening.

Figure 4:
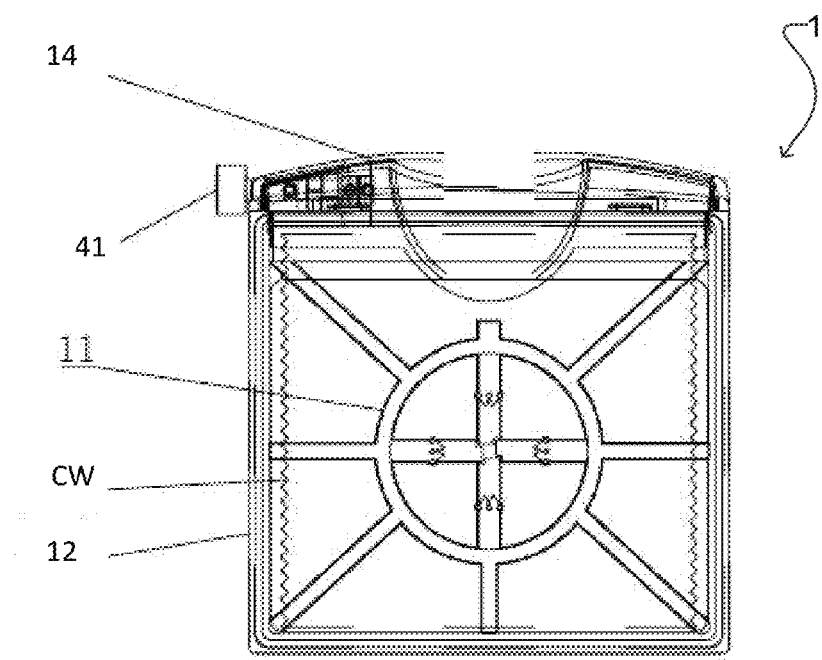
FIG. 4 is a top cutaway view of the embodiment shown in FIG. 1.
Figure 5:
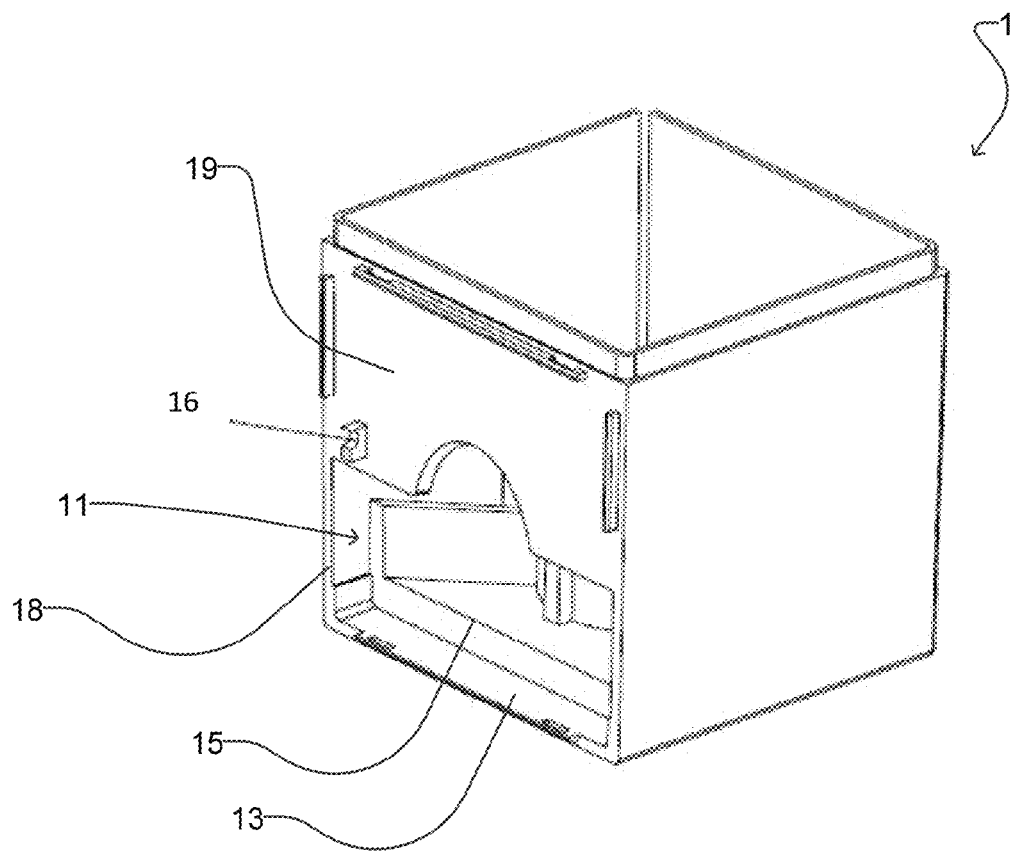
FIG. 5 is a perspective view of the embodiment shown in FIG. 1 with the front panel and top lid removed.
Figure 6:
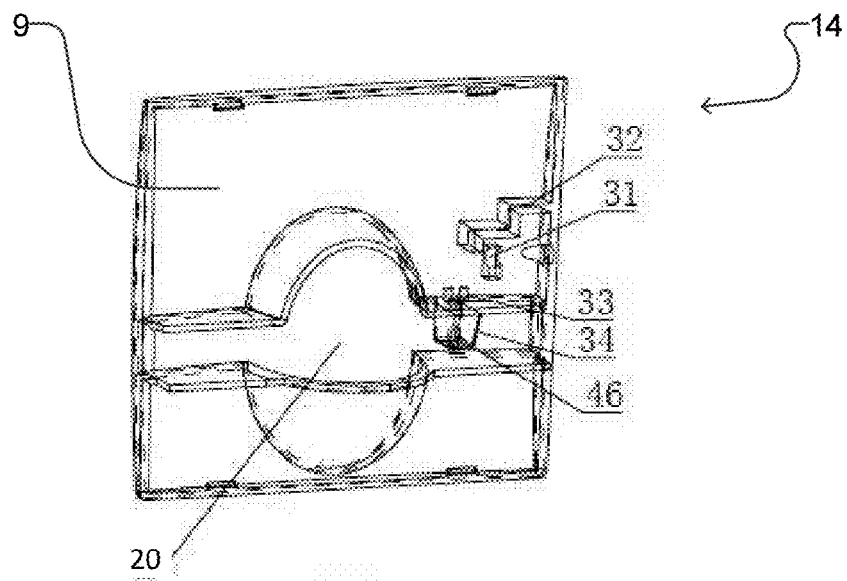
FIG. 6 is a rear view of the front panel of the embodiment shown in FIG. 1 without the knob.
Figure 7:
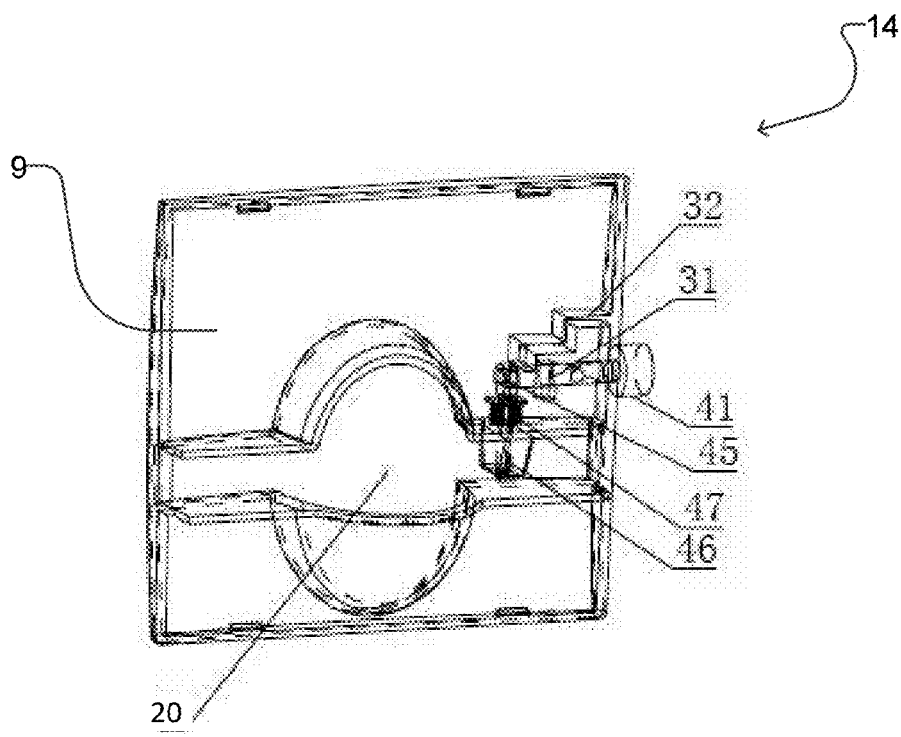
FIG. 7 is a rear view of the front panel of the embodiment shown in FIG. 1 with the knob.
Figure 12:
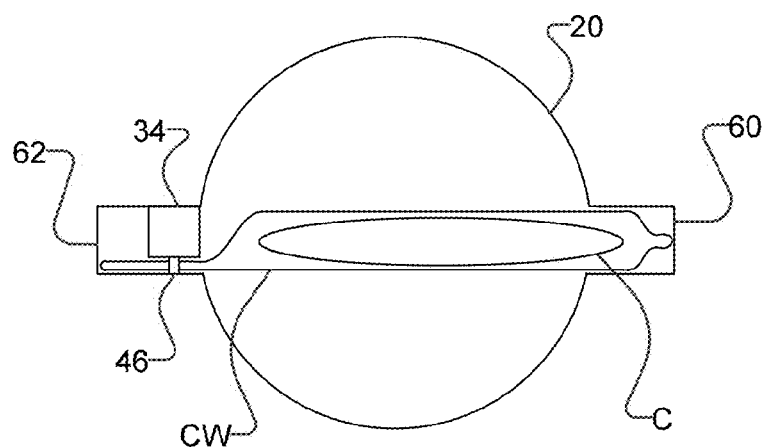
FIG. 12 is a front view of an opening, guide and blade of the embodiments shown in FIG. 1.

Consistent cutting of the edge of condom wrapper CW is also facilitated by the sizing of box 1. As best shown in FIG. 4, the length and width of the interior of box 1 roughly corresponds to the length and width of a standard condom wrapper CW, and the widths of opening 18, 20 roughly corresponds to the width of a standard condom wrapper CW, ensuring condom wrapper CW is pulled out of box 1 in a consistent fashion by the user to ensure blade 46 consistently cuts an identical edge part off of each condom wrapper CW. In particular, as best shown in FIGS. 11 and 12, side walls 60 and 62 of openings 18 and 20 (or only of opening 18 if there is no front panel 14) guide condom wrapper CW through openings 18 and 20 (or only through opening 18 if there is no front panel 14) in a consistent manner as the user withdraws condom wrapper CW in direction D2.

Condom wrappers CW can be stored in a consistent orientation in box 1, ensuring that the opened condom, wrappers CW pulled from box 1 provide condoms in a consistent orientation, obviating the need for handling the condom further (and thereby risk damaging it) to determine correct orientation.

In some embodiments, two cutting assemblies 4 may be provided, one at each side of opening 20 of front panel 14, such that both cutting assemblies 4 can work simultaneously to cut both edges of condom wrapper CW off as it is pulled out of box 1 by a user.

Figure 8:
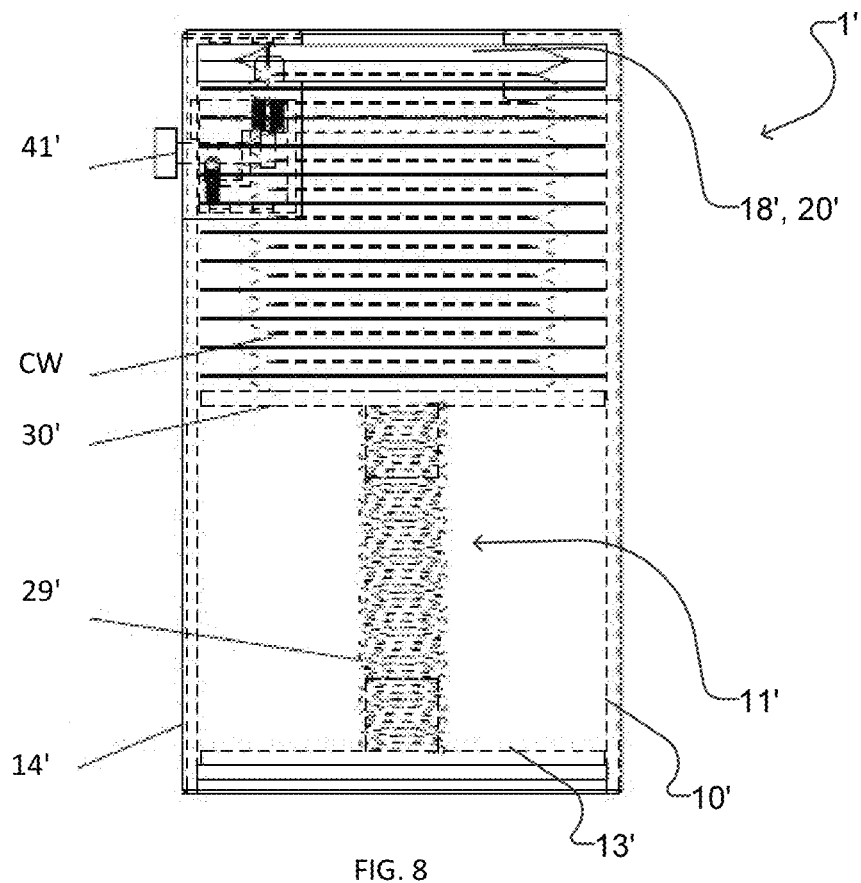
FIG. 8 is a cutaway side view of an apparatus for storing and dispensing condoms according to an embodiment.
Figure 9:
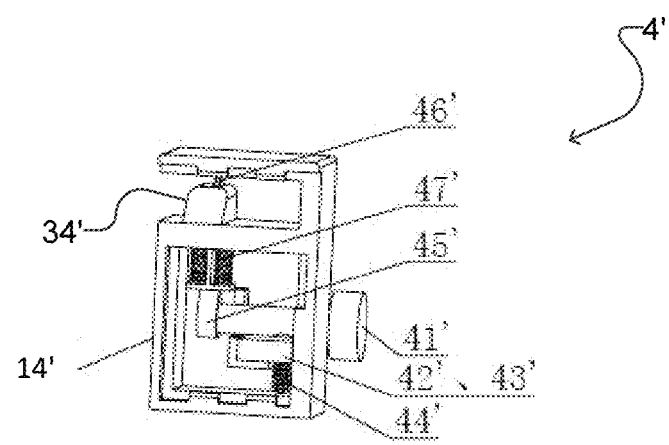
FIG. 9 is front view of the cutting assembly of the embodiment shown in FIG. 8.

FIGS. 8 and 9 shows a box 1' for storing and dispensing condoms according to another embodiment of the invention. As shown in FIG. 8, a base 11' for receiving condom wrappers CW comprises a supporting a supporting spring 29' and a plate 30' fixed to the top of supporting spring 29'. The bottom of the supporting spring 29' is fixed to bottom 13' of body 10'. A plurality of individual condom wrappers CW may be stacked on plate 30'. Opening 18' of body 10' and corresponding opening 20' of front panel 14' are set at respective upper portions of body 10' and front panel 14', and a cutting assembly 4' is disposed adjacent to opening 20'. The structure and function of cutting assembly 4' is similar to cutting assembly 4 of box 1 with correspondingly numbered features having corresponding structure and function, but the cutting orientation of cutting assembly 4' is front bottom to top as shown best in FIG. 9.

This application is intended to cover any variations, uses, or adaptations of the invention using its general principles. Further, this application is intended to cover such departures from, the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

The invention claimed is:

1. An apparatus for storing and dispensing condoms comprising:
   a body comprising
   a base for receiving a stack of condom wrappers;
   an opening for accessing a condom wrapper, the opening comprising a guide adjacent a side of the opening;

a cutting assembly comprising a blade configurable in an extended position for cutting an edge of the condom wrapper as the condom wrapper is pulled through the opening, wherein the guide is configured to deform and/or displace a condom within the condom wrapper laterally away from the blade so that the blade does not cut the condom as the condom wrapper is pulled through the opening, wherein the guide comprising a gap with a gap height less than a thickness of a rolled condom and wherein at least a portion of the gap is closer to a center of the opening than the blade;

wherein the cutting assembly is configurable in a retracted position for avoiding cutting the edge of the condom wrapper as the condom wrapper is pulled through the opening;

wherein the body comprises a front panel, the front panel comprising the opening;

wherein the cutting assembly comprises a knob comprising:
- a head disposed outside the body;
- a barrel fixed to the head and extending into the body through a side aperture of the front panel; and
- a cam fixed to a distal end of the barrel, the cam comprising a bearing surface abutting a proximal end of the blade,
- whereby rotation of the knob configures the blade between the extended position and the retracted position.

2. An apparatus according to claim 1, wherein the barrel comprises a bearing circumference with at least one recess, and the cutting assembly further comprises:

a stop fixed to the front panel and comprising a through hole;

a positioning ball set within the through hole;

a spring for biasing the positioning ball against a bearing circumference of the barrel, the spring comprising a first end bearing against the positioning ball.

3. An apparatus according to claim 2, wherein the spring biases the positioning ball against a recess of the barrel when the knob is rotated to configure the blade at the extended position.

4. An apparatus according to claim 2, wherein the spring biases the positioning ball against a recess of the barrel when the knob is rotated to configure the blade at the retracted position.

5. An apparatus according to claim 2, wherein the bearing circumference comprises two opposed recesses, and the spring biases the positioning ball against a first recess of the barrel when the knob is rotated to configure the blade in the extended position, and against a second recess of the barrel when the knob is rotated to configure the blade in the retracted position.

6. An apparatus according to claim 1, comprising at least one spring for biasing the blade into the retracted position, the at least one spring mounted on a guide post fixed on an inner face of the front panel, wherein a length of the post is less than an uncompressed length of the at least one spring.

7. An apparatus according to claim 1, wherein the blade comprises a tapered shape with a tip, the tip disposed at a side region of the opening of the front panel when the blade is in the extended position.

* * * * *

UNITED STATES PATENT AND TRADEMARK OFFICE
CERTIFICATE OF CORRECTION

PATENT NO. : 9,861,514 B2
APPLICATION NO. : 14/735919
DATED : January 9, 2018
INVENTOR(S) : Victor W. J. Chan et al.

It is certified that error appears in the above-identified patent and that said Letters Patent is hereby corrected as shown below:

On the Title Page

Item (71), "Applicant: Rulin Chen, Guangzhou, Guangdong (CN)" should read
--Applicants: Rulin Chen, Guangzhou, Guangdong (CN); Victor W.J. Chan, Taipo (HK)--

Signed and Sealed this
Tenth Day of April, 2018

Andrei Iancu
*Director of the United States Patent and Trademark Office*